United States Patent [19]

Kagawa

[11] 4,331,826

[45] May 25, 1982

[54] PROCESS FOR SEPARATING P-XYLENE FROM A HYDROCARBON MIXTURE

[75] Inventor: Saburo Kagawa, Akashi, Japan

[73] Assignee: Kawasaki Jukogyo Kabushiki Kaisha, Hyogo, Japan

[21] Appl. No.: 244,479

[22] Filed: Mar. 16, 1981

[30] Foreign Application Priority Data

Mar. 17, 1980 [JP] Japan .................................. 55-32727

[51] Int. Cl.$^3$ .............................................. C07C 7/14
[52] U.S. Cl. .................................... 585/812; 585/816; 585/817
[58] Field of Search ........................ 585/812, 816, 817

[56] References Cited

FOREIGN PATENT DOCUMENTS 768636 2/1957 United Kingdom ................ 585/812

*Primary Examiner*—Thomas A. Waltz
*Assistant Examiner*—A. Pal

*Attorney, Agent, or Firm*—Sughrue, Mion, Zinn, Macpeak and Seas

[57] ABSTRACT

A process and an apparatus therefor are described for separating p-xylene from a p-xylene containing hydrocarbon liquid feed material by crystallization, said process comprising (1) mixing a p-xylene containing hydrocarbon feed material with an inert liquid refrigerant, (2) feeding the mixed liquid into a lower part of a bubble tower type crystallization tower as an ascending current, (3) evaporating the refrigerant by the lowering of the liquid static pressure caused by ascent of the mixed liquid and by the transfer of heat into the refrigerant due to solidification of p-xylene and by the lowering of the temperature of the mixed liquid, cooling the ascending liquid to form a slurry of p-xylene crystals in the hydrocarbon liquid, (4) separating the inert refrigerant as a vapor from the liquid surface of the upper part of the crystallization zone, and (5) separating p-xylene crystals from the slurry discharged from the upper part of the crystallization zone.

7 Claims, 2 Drawing Figures

PROCESS FOR SEPARATING P-XYLENE FROM A HYDROCARBON MIXTURE

FIELD OF THE INVENTION

The present invention relates to a process for separating p-xylene from a hydrocarbon mixture, particularly by crystallization by means of a direct cooling process. More particularly, the present invention relates to a process for separating p-xylene from a p-xylene rich hydrocarbon mixture by crystallization comprising growing p-xylene crystals by fractional crystallization using a direct cooling to achieve improved particle size.

BACKGROUND OF THE INVENTION

Hitherto, known processes for separating p-xylene from a hydrocarbon mixture by crystallization include: (a) a process for crystallizing p-xylene comprising cooling p-xylene containing hydrocarbon liquid with a refrigerant through a heat-transfer face of an evaporator; this is referred to as the indirect cooling process or well scraping process, and is described, for example, in U.S. Pat. No. 283,383; and (b) a process for crystallizing p-xylene comprising cooling by a direct cooling process and a circulation stream process, namely, mixing a p-xylene containing hydrocarbon liquid with an inert liquid refrigerant and volatilizing the mixed refrigerant in the hydrocarbon liquid to cool the hydrocarbon liquid, described, for example, in U.S. Pat. No. 2,533,232. In process (a), the size of p-xylene crystals is small. Consequently, the yield is low because the separation efficiency in the subsequent filtration or centrifugal separation step is undesirably low. Further, since the mother liquor is occluded in the resulting crystal cake (i.e., cavities in the cake are filled with the mother liquor), the purity of p-xylene in the separated cake is low and, consequently, subsequent purification is difficult to achieve.

In the direct cooling-circulation process of (b), a special circulation apparatus is required, because it is necessary to create a large circulation stream. Moreover, it has the fault that a plurality of apparatus must be used in order to produce p-xylene in a large volume, because a single apparatus has a very limited capability.

SUMMARY OF THE INVENTION

The present invention relates to an improved process for separating p-xylene by crystallization by a direct cooling-circulation process. As a result of studies in view of the above described problem with the prior processes, in order to provide an improved process for separating p-xylene by crystallization which has characteristics such that the resulting p-xylene has a large crystal size, the crystal cake does not occlude the mother liquor, a circulation stream and a circulation apparatus are not required, the volume capability of the single apparatus is not severely limited (and, consequently, a plurality of apparatus is not required for production of p-xylene on a large scale), the present invention has now been attained.

Particularly, this invention provides a process comprising (1) mixing a p-xylene containing hydrocarbon feed material with an inert liquid refrigerant, (2) feeding the mixed liquid into a lower part of a bubble tower type crystallization tower as an ascending current, (3) evaporating the refrigerant by the lowering of the liquid static pressure caused by ascent of the mixed liquid and by the transfer of heat into the refrigerant due to solidification of p-xylene and by the lowering of the temperature of the mixed liquid, cooling the ascending liquid to form a slurry of p-xylene crystals in the hydrocarbon liquid, wherein the ascending liquid is continuously cooled by feeding the mixture of the hydrocarbon liquid feed material and the liquid refrigerant so that the temperature of the ascending liquid in each part of the crystallization zone is decreased to gradually approach a vapour-liquid equilibrium temperature of the system to the liquid pressure on each height level of the crystallization zone, thereby promoting growth of p-xylene crystals by maintaining a supercooled state during the crystallization step, while maintaining the crystallization zone at a temperature higher than the temperature at which an eutectic mixture is formed, maintaining a mixed phase stream composed substantially of the hydrocarbon material-p-xylene crystal slurry, the inert liquid refrigerant, and the vapor of the inert refrigerant as the ascending current, (4) separating the inert refrigerant as a vapor from the liquid surface of the upper part of the crystallization zone, and (5) separating p-xylene crystals from the slurry discharged from the upper part of the crystallization zone.

DETAILED DESCRIPTION OF THE INVENTION

Figure 1:
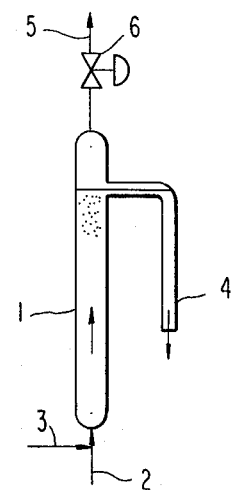
FIG. 1 is a schematic diagram of an example of a bubble tower type crystallization tower used according to this invention.

This invention provides a process comprising (1) mixing a p-xylene containing hydrocarbon feed material with an inert liquid refrigerant, (2) feeding the mixed liquid into a lower part of a bubble tower type crystallization tower as an ascending current, (3) (a) evaporating the refrigerant by the lowering of the liquid static pressure caused by ascent of the mixed liquid and by the transfer of heat into the refrigerant due to solidification of p-xylene and by the lowering of the temperature of the mixed liquid, cooling the ascending liquid to a temperature near the secondary crystallization temperature (eutectic point) to form a slurry of p-xylene crystals in the hydrocarbon liquid, wherein (b) the ascending liquid is continuously cooled by feeding a mixture of the hydrocarbon liquid feed material and the liquid refrigerant so that the temperature of the ascending liquid in each part of the crystallization zone is decreased to gradually approach a vapor-liquid equilibrium temperature of the system to the liquid pressure on each height level of the crystallization zone, thereby (c) promoting growth of p-xylene crystals by maintaining a supercooled state during the crystallization step within very narrow range of temperature difference, (for example, 1° C. or less), keeping the crystallization zone at a temperature higher, preferably less than 10° C. higher, more preferably less than 1° C. higher, and most preferably less than 0.1° C. higher than the temperature at which the eutectic mixture is formed, (d) maintaining a mixed phase stream composed substantially of hydrocarbon material-p-xylene crystal slurry, the inert liquid refrigerant, and vapor of the inert refrigerant as the ascending current, (4) separating the inert refrigerant as a vapor from the liquid surface of the upper part of the crystallization zone, and (5) separating p-xylene crystals from the slurry discharged from the upper part of the crystallization zone.

The feed liquid in the present invention is generally composed of p-xylene rich hydrocarbon compounds, and a preferred feed liquid is a mixture consisting of $C_8$ aromatic hydrocarbons (o-, m- and p-xylene, ethylbenzene, etc.) containing about 10% p-xylene. Industrial xylene mixtures are particularly suitable feed materials, examples of which include a liquid distillate from a coke oven, a liquid distillate from an apparatus for producing ethylene, a fraction prepared by purification of solvents, a $C_8$ aromatic hydrocarbon fraction subjected to a catalytic reaction, and analogous materials.

The inert liquid refrigerant is preferred to have a latent heat of vaporization of at least 30 calories, and preferably from 50 to 100 calories, per gram. Further, it is preferred to use a liquid which can function as a refrigerant by subjecting it to an operation in a low temperature refrigeration cycle at a temperature in the range from about $-35°$ C. to $-144°$ C. under a pressure in the range from 0.1 atmosphere to about 20 atmospheres. The refrigerant used is preferred to show a large variation of saturation pressure with respect to the temperatures used. The term "inert" means that the substrate does not have a chemical reactivity with the system to a perceptible degree, and, particularly, does not have a corrosive action to materials for construction.

Typical useful inert refrigerant includes carbon dioxide, ammonia, lower hydrocarbons such as alkanes having from 2 to 4, and preferably 2 or 3 carbon atoms, for example, methane, ethane, propane and butane, etc., and alkenes having from 2 to 4, and preferably 2 or 3 carbon atoms, for example, ethylene, and propylene, etc., fluorine or chlorine substituted lower hydrocarbons such as Freon, etc., sulfur dioxide and analogous substances.

The eutectic temperature and the pressure of the system at that temperature vary according to the composition of the hydrocarbon liquid feed material and the mixing ratio of the liquid refrigerant. If a pressure under which eutectic crystals begin to form is determined for a feed material having a definite composition, temperature, and pressure, and for a refrigerant having a definite composition, temperature, and pressure, the ratio of the refrigerant to be mixed can be decided at once by calculating a heat balance and a material balance, that is, from the solubility of the p-xylene and the vapor-liquid equilibrium relation between the materials charged in the tower, assuming that the sum of the amounts of out-going materials from the tower is equal to the sum of the amount of incoming materials to the tower and that the sum of heat accompanied by the out-going materials is equal to the sum of heat accompanied by the in-coming materials. The final pressure of the operation, i.e., the pressure at the top of the tower, is preferably in the range of from 0.1 kg/cm$^2$.ab. to 10 kg/cm$^2$.ab. A more preferable range is from 0.2 kg/cm$^2$.ab. to 5 kg/cm$^2$.ab., and most preferable is a pressure from 0.3 kg/cm$^2$.ab. to 1.2 kg/cm$^2$.ab.

The pressure which is the standard for fixing the mixing ratio of the refrigerant (pressure under which eutectic crystals begin to form) may be suitably decided within the above described ranges based on consideration the difficulty of the operation and equipment cost.

The final pressure in a typical practical operation, namely, the pressure of the top part of the crystallization tower, is maintained from 0.01 kg/cm$^2$ to 1 kg/cm$^2$ higher, and preferably from 0.005 kg/cm$^2$ to 0.1 kg/cm$^2$ higher, than the pressure which is the standard for fixing the mixing ratio of the refrigerant, by which the final operation temperature can be kept at a temperature about 0.01° C. higher than the eutectic temperature, although the value may vary according to the particular refrigerant used.

Generally, a mixing ratio by weight of the p-xylene contained in the hydrocarbon feed material and the inert liquid refrigerant, is from 0.05 to 20, preferably 0.1 to 10.

The feed rate of the feed liquor and the refrigerant (rate at the bottom of the tower) is from 2 mm/sec to 30 mm/sec, preferably from 3 mm/sec to 15 mm/sec, and more preferably from 3 mm/sec to 6 mm/sec. Further, it is preferred that the operation be carried out so that rate of decrease of the temperature in the tower is from 0.01° to 1° C./min., preferably from 0.1° to 0.3° C./min., and most preferably from 0.1° to 0.2° C./min.

The effective size of the tower depends upon the content of p-xylene in the feed liquid and the kind of the refrigerant. For example, in the case that the p-xylene content in the feed liquid is from 14% to 23% by weight, a tower having a height of from 25 m to 80 m, preferably 30 m to 60 m would be used, and a tower having a cross-sectional area within a range of from 0.3 m$^2$ to 50 m$^2$, preferably from 0.5 m$^2$ to 25 m$^2$, which is decided depending on the amount of p-xylene to be produced, would be used.

FIG. 1 is a schematic diagram of an example of an apparatus used in the present invention, wherein a feed liquid and an inert liquid refrigerant (referred to as refrigerant hereinafter) are fed as a mixture to the bottom of a bubble tower type crystallization tower 1 (referred to as the tower hereinafter) through conduits 2 and 3. Since there is a static pressure difference corresponding to the liquid head between the top part and the bottom part of the tower 1, the static pressure lowers during ascent of the feed liquid in the tower 1 to cause evaporation of the refrigerant.

The evaporated refrigerant ascends in the tower as bubbles. The liquid and bubbles ascending in the tower 1 form the so-called bubble dispersion phase. The ascending current is stabilized when a gas release value, i.e., a gas hold-up value (volume of gas per unit volume of the gasliquid mixture) is lower than a certain value, and thus there is a substantially constant continuous pressure difference between the top and the bottom of the tower 1.

The vapor-liquid equilibrium temperature can be easily calculated from the pressure of the system, the concentration of each component in the system and the solubility of p-xylene, using the vapor-pressure equilibrium relation. The pressure of each point within a certain horizontal cross section of the tower is nearly equal one another. Further, the temperature of the liquid at each point in a horizontal cross section of the tower 1 is substantially uniform, because the latent heat required for gasification of the refrigerant is supplied with the decrease in the temperature of the mixed liquid.

Further, this temperature is higher than the temperature of the bubbles in the same horizontal cross section of the tower 1 (namely, the vapor-liquid equilibrium temperature of the system to the pressure in each point on the horizontal cross section of the tower 1) so as to have a temperature difference necessary to transfer the latent heat for evaporation.

In a certain range or less of the gas hold-up value, the above described temperature difference is hardly observed, because the ascending flow is uniform and the heat-transfer rate from the mixed liquid to the refrigerant just before evaporation is very large. Since the relation between the vapor-liquid equilibrium temperature and pressure in such a system can generally be approximated as a function of the first degree, the temperature of the ascending current in the tower 1 continuously gradually reduces as ascending.

An operation temperature of the top of the tower 1 can be controlled by a pressure controlling valve, and the operation temperature of each horizontal cross section in the tower 1 can be easily controlled within a tolerance range of mutual relations of the height of the tower, the density of the liquid and the relation of vapor-liquid equilibrium temperature-pressure of the system.

In the tower 1 shown in FIG. 1 wherein the height is determined so as to maintain a liquid static pressure corresponding to a difference between the vapor-liquid equilibrium pressure of the system at a temperature higher than the initial crystallization point (primary crystallization temperature) of the feed liquor and the vapor-liquid equilibrium pressure of the system at the eutectic point (secondary crystallization temperature) of the feed materials, the feed liquor and the refrigerant are mixed in a suitable ratio (the amount of the refrigerant being necessary to cool the feed material to a temperature near the eutectic point from the feed temperature) at a temperature higher than the initial crystallization point, and the mixture is continuously fed to the bottom of the tower 1. The eutectic point (secondary crystallization temperature) is a temperature wherein the secondary component having a lower solidifying point than the primary component deposits after the solidification of the primary component when the temperature lowers in a solution containing many ingredients, and below the eutectic point the deposited secondary component is present together with the deposited primary component (eutectic mixture). It is preferred that the pressure of this mixed liquid is at least equal to or somewhat higher than the vapor-liquid equilibrium pressure to the temperature of the mixed liquid.

The mixed liquid fed ascends in the tower 1, while the pressure gradually decreases as ascending the mixed liquid. When the mixed liquid reaches the vapor-liquid equilibrium pressure of the system, the refrigerant starts to evaporate, and thereafter the refrigerant ascends together with the feed liquor while evaporating. The pressure-temperature relation in the system is kept at the vapor-liquid equilibrium relation and the evaporation amount of the refrigerant is controlled by the heat supplied to the refrigerant.

Particularly, the evaporation amount is limited to an amount corresponding to the heat supplied by the temperature drop of the system. The temperature of the system gradually decreases ascending of the mixed liquid, and when the temperature reaches to the initial crystallization point of the feed liquor, p-xylene starts to crystalline. The separated crystals ascend together with the liquid without descending, in case that the liquid ascending rate is in a range that the sum of the buoyancy of the crystal and the liquid resistance is larger than the weight of the crystal.

Subsequently, the amount of separated crystals of p-xylene increases as the temperature decreases. Formation of new crystals and growth of the crystals are continued to form a mixed stream composed of a p-xylene slurry and bubbles, and the stream reaches to the top of the tower 1. The liquid reaching to the top of the tower is discharged by overflowing by means of a discharge conduit for the slurry liquid 4 to form a liquid surface. The evaporated refrigerant is separated at the liquid surface, and discharged from a discharge conduit for vapor of the refrigerant 5.

The pressure of the top of the tower can be controlled by controlling the amount of the refrigerant to be mixed or by means of a pressure controlling valve 6, by which the refrigerant can be evaporated in a necessary amount, and the temperature of the slurry liquid at the top of the tower is maintained at a temperature slightly higher than the eutectic point of the feed liquid, namely, a temperature which is from 0.01° to 10° C. higher, and preferably from 0.01° C. to 1° C. higher. The discharged slurry liquid is sent to a centrifugal separation step and a purification step, and the vapor of the refrigerant is sent to a compression step of the refrigeration cycle.

Figure 2:
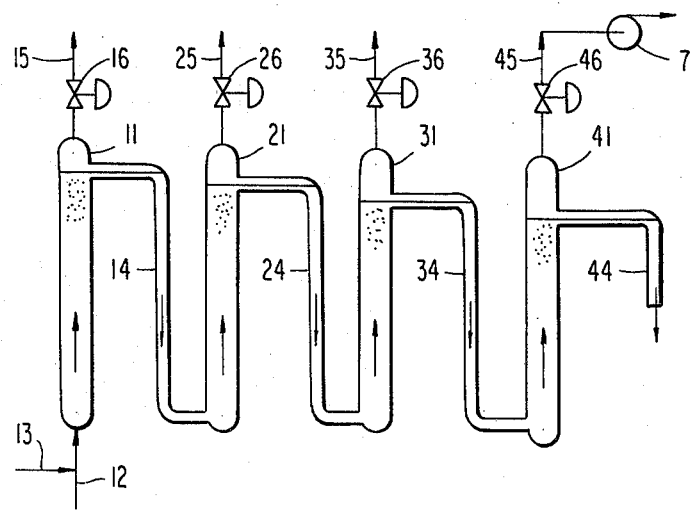
FIG. 2 is a schematic diagram of another examples, having four crystallization towers, according to this invention.

FIG. 2 is a schematic diagram of an embodiment of the invention for use in a case wherein $C_8$ (eight carbon atoms) aromatic hydrocarbon compounds (such as p-xylene) are used as the feed liquid, and, for example, ethylene is used as the refrigerant.

In this case, since the effective height of the tower required is, for instance, 45.1 m for a feed liquid containing 20% p-xylene, the tower is divided into 4 towers from the view point of facility of production and installation of the apparatus. The operation of each tower is in principle the same as that of the case shown in FIG. 1, but the following differences are noted:

(a) The temperature of the bottom of the tower is higher than the initial crystallization point in only the first tower 11 and lower than the initial crystallization point in the second tower 21, the third tower 31 and the fourth tower 41. The overflowing liquids discharged from the discharge conduit for the slurry liquid produced 14, 24 and 34 in the first tower 11, the second tower 21 and the third tower 31 are fed to the bottoms of the second tower 21, the third tower 31 and the fourth tower 41, respectively, and the refrigerant is fed to the bottom of the first tower through a conduit 13.

(b) The temperature of the top of the tower is near the eutectic point in only the fourth tower 41, and the temperatures of the top of the first tower, the second tower and the third tower are between the initial crystallization point and the eutectic point.

(c) The mixing ratio of the refrigerant to the feed liquid in the first tower, the second tower, and the third tower is determined based on the amount of the refrigerant sufficient to keep the pressure-temperature relation of the top of each tower (pressure depends on the effective height of the tower) at a vapor-liquid equilibrium relation. The sum total of amounts of the refrigerant fed to each tower is an amount necessary to keep the feed liquid at a temperature near the eutectic point.

(d) The sum of the effective heights of each tower is determined so that it is equal to the effective height of a single taller tower as is shown in FIG. 1.

In spite of the above described differences, the first, the second, the third and the fourth towers are regarded as one-system, and there is not any substantial difference therein from the case shown in FIG. 1 except that the evaporated refrigerant is separated at several points on the path the ascending current. However, the essential requisites for the embodiment of FIG. 2 of the invention are completely similar to the case shown in FIG. 1, wherein the pressure reduces during ascent of the liquid, and cooling and crystallization gradually proceed continuously while the temperature at a vapor-liquid equilibrium relation.

However, the dividing into plural parts does bring about a preferred result in that the amount of ascending bubbles in a certain zone is decreased, to thereby reduce the necessary cross-sectional area in the zone, because of the separation on the path of evaporation and cooling.

EXAMPLE 1

To the apparatus shown in FIG. 1, a $C_8$ aromatic rich hydrocarbon having the following composition was fed as a raw material, and ethylene was fed as a refrigerant:

| | |
|---|---|
| p-Xylene | 8.6% by weight |
| m-Xylene | 47.4% by weight |
| o-Xylene | 22.0% by weight |
| Ethylbenzene | 19.8% by weight |
| Other hydrocarbons | 2.2% by weight |

These were continuously fed to the bottom of the crystallization tower 1 having the effective height of about 11.0 m through conduits 2 and 3, respectively, in a ratio by weight of liquid ethylene to feed liquid of about 0.132. The temperature was about $-73°$ C. and the pressure was about 3.0 kg/cm$^2$.ab. As a result of calculation, the initial crystallization point was determined to be about $-72°$ C. When the pressure of the top of the tower was controlled to about 1.04 kg/cm$^2$.ab. by means of the pressure controlling valve 6, the temperature was about $-80°$ C.

Ethylene vapor separating from the top of the tower was discharged out of the system through the conduit 5, the amount ratio by weight of which was 0.102 based on the feed liquid. The liquid feed rate to the tower was kept at about 18 m$^3$ per hour based on 1 m$^2$ of the tower section area by controlling the feed amounts of the feed liquid and the refrigerant.

Crystals contained in the slurry liquid obtained from the top of the tower were plate-like crystals having sizes of about 400 to 600$\mu$ in width.

EXAMPLE 2

An apparatus as in FIG. 2, a $C_8$ aromatic-rich hydrocarbon having the following composition, and ethylene as a refrigerant, were used. Composition of the feed liquid:

| | |
|---|---|
| p-Xylene | 20% by weight |
| m-Xylene | 43% by weight |
| o-Xylene | 20% by weight |
| Ethylbenzene | 15% by weight |
| Other hydrocarbons | 2% by weight |

The effective height of the first tower, namely, the crystallization tower 11, was 20.5 m, that of the second tower, namely, the crystallization tower 21, was about 15 m, that of the third tower, namely, the crystallization tower 31, was about 6 m, and that of the fourth tower, namely, the crystallization tower 41 was about 3.6 m. The towers each had the same inside diameter, which was about 480 mm.

To the bottom of the first tower 11, the feed liquid and refrigerant were fed continuously through the conduits 12 and 13, respectively, in a ratio by weight of the liquid ethylene to the feed liquid of about 0.172. The temperature thereof was about $-52°$ C. and the pressure was about 6.0 kg/cm$^2$.ab. As a result of calculation, the initial crystallization point was determined to be about $-54°$ C.

The pressure of the top of the first tower 11 was therefore controlled so as to be about 2.5 kg/cm$^2$-ab. by the pressure controlling valve 16. The temperature in this case was about $-60.5°$ C.

The pressure of the top of the second tower 21 was controlled so as to be about 1.3 kg/cm$^2$-ab. by the pressure controlling valve 26. The temperature in this case was about $-68°$ C.

The pressure of the top of the third tower 31 was controlled so as to be about 0.8 kg/cm$^2$-ab by the pressure controlling valve 36. The temperature in this case was about $-72°$ C.

The pressure of the top of the fourth tower 41 was controlled so as to be about 0.5 kg/cm$^2$-ab. by the pressure controlling valve 46. The temperature in this case was about $-74.5°$ C. Ethylene vapor separated from the top of each tower was discharged out of the system through conduits 15, 25, 35 and 45, the amounts of which were about 0.072, 0.042, 0.020 and 0.013, based on the weight of the feed liquid fed to the first tower.

The feed rate in the first tower 11 was kept at about 19-20 m$^3$/hour, based on 1 m$^2$ of the tower section area, by controlling feed amounts of the raw material and the refrigerant.

Crystals obtained from the fourth tower were plate-like crystals and had sizes in the range of about 400-700$\mu$ in width, which is remarkably large as compared with the average size of about 100-300$\mu$ of p-xylene crystals obtained by the conventional indirect cooling process.

EXAMPLE 3

In the following, an example wherein a $C_8$ aromatic-rich hydrocarbon having the following composition and ethylene as the refrigerant were used is shown. The same apparatus as in Example 2 was used. Composition of the feed liquid:

| | |
|---|---|
| p-Xylene | 17% by weight |
| m-Xylene | 43% by weight |
| o-Xylene | 20% by weight |
| Ethylbenzene | 18% by weight |
| Other hydrocarbons | 2% by weight |

To the bottom of the first tower 11, they were fed continuously through the conduits 12 and 13, respectively, in a ratio by weight of the liquid ethylene to the feed liquid of about 0.166. The temperature of both of them was about $-50°$ C. and the pressure was about 6.0 kg/cm$^2$-ab. As a result of calculation, the initial crystallization point was about $-57°$ C.

The pressure of the top of the first tower 11 was controlled so as to be about 2.5 kg/cm$^2$-ab. by the pressure controlling valve 16. The temperature in this case was about $-61°$ C.

The pressure of the top of the second tower 21 was controlled so as to be about 1.3 kg/cm$^2$-ab. by the pressure controlling valve 26. The temperature in this case was about −68.5° C.

The pressure of the top of the third tower 31 was controlled so as to be about 0.8 kg/cm$^2$-ab. by the pressure controlling valve 36. The temperature in this case was about −72° C.

The pressure of the top of the fourth tower 41 was controlled so as to be about 0.5 kg/cm$^2$-ab. by the pressure controlling valve 46. The temperature in this case was about −75.5° C. Ethylene vapor separated from the top of each tower was discharged out of the system through conduits 15, 25, 35, and 45, the amounts of which were about 0.060, 0.046, 0.021 and 0.013 based on the weight of the feed liquid fed to the first tower.

The amount of crystals separated in the first tower was small as compared with that in Example 2, because the p-xylene content in the raw material was low. The feed temperature was set so as to economically recover cooling heat from a filtrate in the subsequent purification step.

In this sense, the first tower has the character of a precooling tower. However, the precooling may be carried out by other methods, for example, the feed liquid may be precooled indirectly by a heat exchanger to a temperature slightly higher than the initial crystallization point.

Further, the first tower also has a characteristic that variation of the composition of the raw material, particularly, variation of p-xylene content and m-xylene or o-xylene content observed in operation of a conventional p-xylene separation apparatus can be compensated for in the first tower.

That is, if the composition of the feed liquid varies, the temperature of the top of the fourth tower 41 can be easily reduced to a temperature near the eutectic point by controlling the amount of the refrigerant and pressure of the top of each tower.

The feed rate in the first tower 11 was kept at about 18–19 m$^3$/hour based on 1 m$^2$ of the tower section area by controlling feed amounts of the raw material and the refrigerant.

Crystals obtained from the fourth tower 41 were plate-like crystals which had nearly the same size as in the case of Example 2.

EXAMPLE 4 p-Xylene content in a feed liquid and influence thereof by a cooling rate were examined using the apparatus shown in FIG. 2. However, the results shown in No. 3 of Table 2 were obtained by adding another tower having the effective height of about 20 m as the primary tower before the apparatus used in Example 2.

The feed liquid was the same as that in Example 1, except that p-xylene was added in a suitable amount to vary the p-xylene content in the range of from 30 to 17% by weight.

The initial crystallization point varied according to the p-xylene content in the feed liquid, but the temperature of the top of the fourth tower was kept at a temperature slightly higher than the eutectic point by controlling the pressure of the top of each tower and the amount of the refrigerant mixed.

The resulted p-xylene slurry was processed for separation by a screen bowl type centrifugal separator at a slurry feed rate of from about 50 to 150 kg/hr and a centrifugal force of from about 2000 to 3000 times of the weight. In order to examine the known fact that the size of crystals becomes large as the cooling rate decreases, the cooling rate after reaching to the initial crystallization point was varied in the range of 0.3° C./min–0.1° C./min. The difference between the final cooling temperature of the slurry and the eutectic point thereof was within about 1° C.

The relation between the cooling rate and purity of p-xyelene in the dried cake separated by the centrifugal separator is shown in Table 1. In every case, the p-xylene content in the feed material was 20%.

TABLE 1

| No. | 1 | 2 | 3 |
|---|---|---|---|
| Average liquid cooling rate (°C./min) | 0.1 | 0.2 | 0.3 |
| Purity of dried cake (% by weight of p-xylene) | 92.5 | 91 | 90 |
| Yield | 0.735 | 0.731 | 0.724 |

The relation between p-xylene content in the feed liquid and purity of p-xylene in the dried cake is shown in Table 2. The cooling rate of the feed liquid was about 0.15° C./min in every case.

TABLE 2

| No. | 1 | 2 | 3 |
|---|---|---|---|
| p-Xylene content in feed liquid (% by weight) | 17 | 20 | 30 |
| Purity of dried cake (% by weight of p-xylene) | 89 | 90.5 | 92.5 |
| Yield | 0.693 | 0.731 | 0.784 |

In the above Tables 1 and 2, "yield" represents a weight ratio of p-xylene obtained in a unit time from the dried cake separated by the centrifugal separator, to p-xylene introduced in a unit time in the feed liquid charged in the bottom of the tower.

In the results shown in Tables 1 and 2, the fact that the purity of p-xylene in the dried cake becomes higher as the cooling rate decreased resulted from the fact that sufficient time is available for the growth of crystals to be carried out, and the fact that the purity of p-xylene in the dried cake becomes higher as the p-xylene content in the feed liquid increases (which means a high initial crystallization point) results from the fact that crystals having a large size can be obtained because a sufficient time for growth is available.

In the following, the beneficial effects by the present invention are summarized:

(i) The purity and the yield of p-xylene in the dried cake are high, because crystals of p-xylene obtained by the present invention have a large size by which the amount of the mother liquor occluded becomes remarkably small.

(ii) As be obvious from FIGS. 1 and 2, there is no circulation stream in the present invention.

(iii) An apparatus having the maximum scale for industrial production of p-xylene (100,000–150,000 tons/year) can be produced as a single system in the light of practical operation conditions for the bubble towers.

While the invention has been described in detail and with reference to specific embodiments thereof, it will be apparent to on skilled in the art that various changes and modifications can be made therein without departing from the spirit and scope thereof.

What is claimed is:

1. A process for separating p-xylene from a p-xylene containing hydrocarbon liquid feed material by crystallization, said process comprising (1) mixing a p-xylene containing hydrocarbon feed material with an inert liquid refrigerant, (2) feeding the mixed liquid into a lower part of a bubble tower type crystallization tower as an ascending current, (3) evaporating the refrigerant by the lowering of the liquid static pressure caused by ascent of the mixed liquid and by the transfer of heat into the refrigerant due to solidification of p-xylene and by the lowering of the temperature of the mixed liquid, cooling the ascending liquid to form a slurry of p-xylene crystals in the hydrocarbon liquid, wherein the ascending liquid is continuously cooled by feeding the mixture of the hydrocarbon liquid feed material and the liquid refrigerant so that the temperature of the ascending liquid in each part of the crystallization zone is decreased to gradually approach a vapor-liquid equilibrium temperature of the system to the liquid pressure on each height level of the crystallization zone, thereby promoting growth of p-xylene crystals by maintaining a supercooled state during the crystallization step, while maintaining the crystallization zone at a temperature higher than the temperature at which an eutectic mixture is formed, maintaining a mixed phase stream composed substantially of the hydrocarbon material-p-xylene crystal slurry, the inert liquid refrigerant, and the vapor of the inert refrigerant as the ascending current, (4) separating the inert refrigerant as a vapor from the liquid surface of the upper part of the crystallization zone, and (5) separating p-xylene crystals from the slurry discharged from the upper part of the crystallization zone.

2. A process according to claim 1, wherein the inert liquid refrigerant has a latent heat of at least 30 calories per gram.

3. A process according to claim 1, wherein the mixing ratio, by weight, of the p-xylene contained in the hydrocarbon liquid feed material and the inert liquid refrigerant, is from 0.1 to 10.

4. A process according to claim 1, wherein the rate of decrease of the temperature of the ascending liquid is from 0.01° C./min to 1° C./min.

5. A process according to claim 1, wherein the inert liquid refrigerant has a latent heat of from 50 to 100 calories per gram.

6. A process according to claim 1, 2, or 5, wherein the inert liquid refrigerant can function in a low temperature refrigeration cycle at a temperature of from about $-35°$ C. to $-140°$ C. under a pressure of from 0.1 atmosphere to about 20 atmospheres.

7. A process according to claim 1, wherein the inert liquid refrigerant is selected from the group consisting of carbon dioxide, ammonia, lower hydrocarbons, fluorine or chlorine substituted lower hydrocarbons, and sulfur dioxide.

* * * * *